United States Patent [19]

Pethö

[11] Patent Number: 4,958,649
[45] Date of Patent: Sep. 25, 1990

[54] APPARATUS FOR TREATING ARTICLES WITH A GASEOUS AND/OR LIQUID MEDIUM

[75] Inventor: Lajos Pethö, Limoges, France
[73] Assignee: Kabivitrum AB, Stockholm, Sweden
[21] Appl. No.: 424,234
[22] PCT Filed: Feb. 9, 1989
[86] PCT No.: PCT/SE89/00052
  § 371 Date: Oct. 16, 1989
  § 102(e) Date: Oct. 16, 1989
[87] PCT Pub. No.: WO89/07457
  PCT Pub. Date: Aug. 24, 1989

[30] Foreign Application Priority Data

Feb. 16, 1988 [SE] Sweden .................................. 8800525

[51] Int. Cl.⁵ .............................................. B08B 3/00
[52] U.S. Cl. ..................................... 134/159; 134/132;
  134/157; 198/803.14; 414/219
[58] Field of Search ............... 134/132, 140, 149, 157,
  134/159, 162; 414/219, 220; 198/803.14, 793,
  797, 800, 802

[56] References Cited

U.S. PATENT DOCUMENTS 2,119,191  5/1938  Wilkinson et al. .................. 134/132
3,292,775  12/1966  White ............................... 134/132 X
4,536,121  8/1985  Stewart et al. ..................... 414/219

FOREIGN PATENT DOCUMENTS 1032975  6/1966  United Kingdom ................ 414/219

Primary Examiner—H. Grant Skaggs
Assistant Examiner—Keith L. Dixon
Attorney, Agent, or Firm—Pollock, Vande Sande & Priddy

[57] ABSTRACT

The present invention relates to an apparatus for treating a plurality of articles with a gaseous or liquid medium. The apparatus includes a cylindrical chamber in which the articles (14) are arranged in an ordered array in channels (16) which are configured on one or more circular plates (13) and which have substantially the form of evolvent lines which extend from the center of the plates to the periphery thereof. The plates (13) are rotatable about a horizontal shaft or axis (25) extending concentrically with the chamber, so that the articles can be successively introduced into or removed from the channels (16). A plurality of plates can be combined to form a plate pack, which is arranged for stepwise axial movement in the chamber.

The apparatus is particularly suited for washing and sterilizing stoppers and capsules or caps used for sealing bottles and other containers, and the invention also relates to the use of the apparatus for this purpose.

7 Claims, 3 Drawing Sheets

APPARATUS FOR TREATING ARTICLES WITH A GASEOUS AND/OR LIQUID MEDIUM

The present invention relates to an apparatus for treating articles or objects with a gaseous and/or liquid medium. More specifically, the invention relates to an apparatus for treating a plurality of mutually similar objects or articles simultaneously, and particularly, but not exclusively, to an apparatus for washing and/or sterilizing various kinds of articles intended for use in the food production and processing industry and the pharmaceutical industry, e.g. such articles as stoppers and/or capsules, including caps, which are intended for subsequent use in sealing such containers as bottles, cans, flasks, hollow tubes, under sterile conditions. The invention also relates to such use of the inventive apparatus.

When bottles are filled with preparations which are intended to be sterile when used, for instance pharmaceutical preparations and preparations intended for infusion, the bottles are preferably sealed with sterile stoppers and/or capsules, caps. When the filled bottles cannot suitably be heat-sterilized, because the preparation concerned is unable to tolerate heat, the preparation may be sterilized initially and then poured into initially sterile containers under sterile conditions. When adopting this procedure, it is absolutely necessary that the stoppers, capsules or caps used to seal the containers are themselves sterile when sealing said containers. The bottles are normally sealed with the aid of both stoppers and capsules, the latter protecting the stoppers against contamination.

Before sealing a bottle with a sterile stopper in a machine intended herefor, it is necessary to pass the stopper through a number of treatment stages. For instance, it is suitable to sort the stoppers for the purpose of removing those stoppers which are wrongly dimensioned or deformed. The stoppers are also washed and sterilized, normally with hot water and steam under high pressure, at a temperature of at least 120° C., so as to ensure that all contaminating microorganisms and spores are killed.

Furthermore, it is necessary to position the stoppers in a suitable stopper-positioning device, prior to introducing the stoppers into the bottle sealing apparatus.

The stoppers are particularly sensitive to mechanical manipulating forces during the sterilizing process, since the rubber material from which the stoppers are composed is relatively soft at high temperatures.

All open handling of the sterilized stoppers creates a risk of re-contaminating the stoppers with microorganisms and spores.

A number of stopper and/or capsule washing and sterilizing apparatus are known to and used in the art. These known apparatus, however, are all encumbered with a number of drawbacks. For instance, if a stopper handling plant is to have a sufficiently high capacity, the stopper and/or capsule washing and sterilizing apparatus used in conjunction therewith will often be extremely space consuming, complicated and expensive. Neither has it been possible with known apparatus to maintain the positions of the stoppers or capsules and caps during the washing and sterilizing process up to the point at which stoppering and/or capsulating of the bottles has been completed, and consequently it has been necessary to position the stoppers in a subsequent stage, therewith incurring the aforesaid risk of mechanical damage to the stoppers and microbial contamination of the stoppers or capsules. Another drawback is that it is not always possible to wash and sterilize the stoppers under sufficiently gentle conditions which will ensure that the stoppers and capsules will be protected from mechanical damage during the process.

The aforementioned drawbacks are eliminated by means of the present invention, which provides a stopper or capsule (cap) washing and sterilizing apparatus of considerable capacity while requiring only a small amount of space and which is of simple construction and therewith relatively inexpensive. The apparatus enables the stoppers or capsules to be handled gently both before, during and after the washing and sterilizing process. The apparatus will also retain the stoppers in their original position during the whole of the treatment process and provides a fully continuous, uninterrupted handling of the stoppers up to the stoppering station.

In accordance with the present invention in its widest aspect, these advantages are achieved with an apparatus for treating simultaneously a plurality of articles with a gaseous and/or liquid medium, the apparatus including a chamber, which has substantially the form of a cylinder having a horizontal axis and which is provided with an -article- inlet and an article outlet, and further including at least one holder device mounted in the chamber and effective in securing an ordered array of articles to be treated. The inventive apparatus is characterized in that the holder device has the form of a circular plate which is provided with guide means so mounted that the articles are arranged on the plate along evolvent lines extending from the centre of the plate to the periphery thereof.

The plate or plates is/are mounted for rotation about an axis which is concentrical with the cylindrical chamber and perpendicular to the plate or plates. The guide means comprise partition walls which are arranged on the plate or plates in a manner to define channels in which the said articles are positioned in rows along the evolvent lines.

The plate, or plates, is/are arranged for stepwise rotation, so that one channel at a time is brought into line with the article inlet or article outlet. The plate, or plates, is, or are, also capable of being rotated during the washing, sterilizing process or during some other treatment process to which the articles are subjected subsequent to being introduced into the channels on the plate or plates. This rotation may be a stepwise or continuous rotation.

Since the axis of rotation of the plate or plates is essentially horizontal, the plate, or plates, will be located substantially vertically. Thus, one plate will form a side wall in those channels formed by the partition walls. In accordance with one preferred embodiment of the invention, a plurality of plates are combined to form a plate pack having a common axis, in a manner such that the side of a plate remote from the partition walls will form the other side wall of the channels defined on a following plate. At the end of the plate pack, where the channels are exposed, these channels will be covered with a plate which has the same size as the remaining plates but which is not provided with the aforesaid partition walls.

When the inventive apparatus includes a plurality of plates which are combined to form a plate pack, the apparatus will also be provided with means for indexing the plate pack in an axial direction, each step moved by the plate pack corresponding to the space or distance between two mutually sequential plates.

Provided on the inner surface of the chamber are means for controlling the stepwise rotation of the plate or plates and for fixating the plates in an axial direction during rotation. In accordance with one preferred embodiment, these means have the form of peripherally extending, mutually parallel ribs which protrude outwards from the inner wall of the chamber. The number of parallel ribs provided will normally be equal to the number of plates included in the plate pack. The plates are in connection with the ribs and rotationally guided thereby, through the agency of a dogging element mounted on the plates.

When the inventive apparatus includes a plurality of plates, the ribs will also incorporate one or more recesses. Each of the ribs will include mutually the same number of recesses and the recesses in said ribs are mutually arranged in said ribs in a manner such that in the array of ribs there will be one or more axially extending regions which are free from ribs. Thus, when the dogging element connected to the plates is located opposite one such recess, the dogging element will thus lie out of engagement with the ribs and can then, instead, be in engagement with an operating device effective in moving the dogging element, and therewith the plates connected thereto, in an axial direction so as to come into engagement with a following rib. This enables the channels in a following plate to be brought into line with the article inlet or outlet.

For the purpose of preventing articles from falling from the channels as the plates rotate, and therewith impeding the function of the apparatus, for instance by being jammed between tha plate pack and the inner wall of the chamber, the apparatus is also provided with barrier means which block the peripheral opening of each of the channels which are not at that time intended to receive an article or to have an article removed therefrom. Such barrier means may, for instance, comprise a multiple of barrier rods which extend through holes in each plate at the edge thereof adjacent the peripheral opening of each of the channels, and therewith prevent entry into said channels. When an article is to be introduced into or removed from a channel, the corresponding barrier rod is withdrawn to an extent such as to expose the peripheral opening of the channel. When a plurality of plates are combined to form a plate pack, the holes located adjacent respective channel openings are arranged in line, so as to enable a barrier rod to be moved axially through the holes in all plates at the peripheral openings of the channels arranged sequentially in the axial direction. The barrier rod can the be withdrawn to an extent which will expose the peripheral opening of the channel into which the article is to be introduced or from which an article is to be removed. Naturally, there is no need to block the opening of those channels which do not contain an article. It will also be understood that the number of barrier rods required will equal the number of channels in each plate.

The invention is described in more detail in the following description, which is made with reference to the accompanying drawings. Described and illustrated is an exemplifying embodiment of a bottle stopper washing and sterilizing apparatus, although it will be understood that the invention is not restricted to this particular use of the inventive apparatus.

In the drawings, FIG. 1 illustrates an apparatus constructed in accordance with the invention, partly in cross-section.

Figure 1:
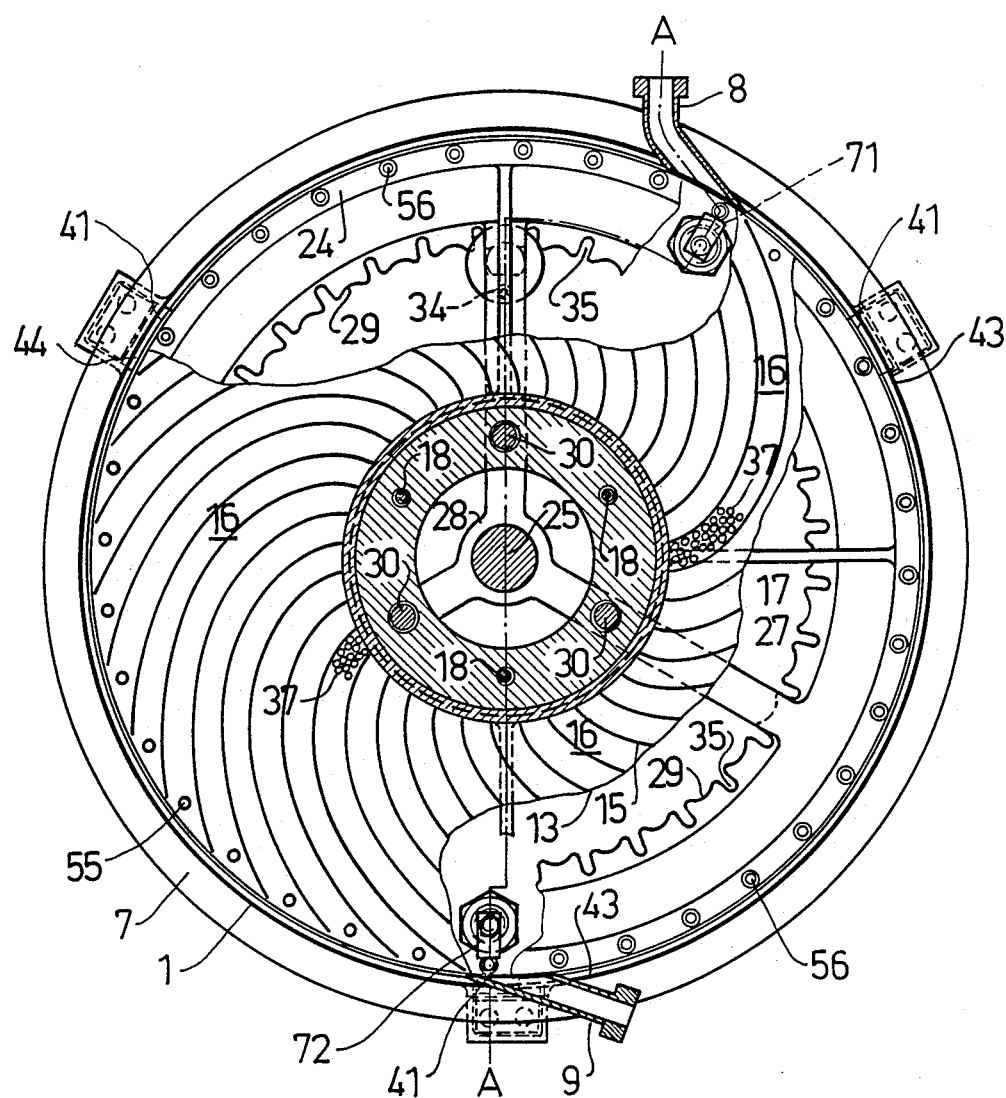

The apparatus illustrated in the drawings includes a cylindrical chamber, which may be divided into two parts 1 and 2. The chamber is also provided with two end walls 3 and 4. The various parts of the chamber are joined together by means of flange connectors 5, 6 and 7, which provide a gas-tight connection between the chamber parts. The chamber also has a stopper inlet opening 8 and a stopper outlet opening 9, and is also provided with further connections 10, 11 and 12 for the delivery and discharge of washing liquid and sterilizing steam.

Arranged in the chamber is a plurality of plates 13 which are intended to support an ordered array of stoppers 14. To this end, the plates are provided with partition walls 15, and it will be seen from FIG. 1 and FIG. 3 that these partition walls, together with the plate, define channels 16 which extend from the centre of the plate out to the periphery thereof, along evolvent lines. Each of the plates has a more robust, annular hub part 17, and a plurality of plates are combined to form a plate pack, which is held together by bolts 18 which pass through the hub part. This will also prevent the plates from rotating relative to one another. The plate pack also includes, on one side thereof, an annular pressure plate 19 which is located adjacent the periphery of the plate pack and which is connected to a hub part 21 by means of radial spokes 20. Arranged on the other side of the plate pack is a further pressure plate 22 which has a central hub part 23 and a peripheral, annular part 24. The side of the pressure plate facing towards the plate pack is smooth and forms a side wall for the channels configured on the adjacent plate. The two pressure plates 19 and 22, together with the bolts 18, bind the plate pack so as to form a solid unit or assembly.

The plate pack can be rotated around the central shaft 25. To this end, a hub 26 is mounted on the shaft 25 on one side of the plate pack and a drive wheel 27 having a hub 28 and a gear ring 29 for driving the hub 28 on the other side of the plate pack. The hub 26 and the drive wheel 27 are fixedly connected to the shaft 25 and are mutually held together by means of bolts 30 which extend through the hub parts 17 of the plates but which are not fixedly connected thereto. The plate pack will therefore be forced to accompany rotational movement of the drive wheel 27 while being capable of axial movement along the bolts 30. The shaft 25 is journalled in journal bearings 31, 32, mounted on the chamber end walls 3 and 4.

The drive wheel 27 and the plate pack connected thereto are caused to rotate by activation of the internal gear ring 29. Since this rotation will preferably be a stepwise rotation, the gear ring 29 is preferably configured as a part of a maltese cross mechanism, which is driven by means of the drive shaft 33, which has a drive pin 34 provided at one end thereof. When the drive shaft is rotated through one revolution, the drive pin 34 will engage an indent 35 in the gear ring 29, such as to rotate the drive wheel forwards through one step. It will be understood, however, that the gear ring 29 may also be provided with conventional, internal teeth, in which case the drive shaft 33 will be provided with a conventional gear wheel and be driven by a conventional, known stepping motor.

The drive shaft 33 extends through a sealing lead-through or bushing mounted in the chamber end wall 4 and may be driven by an external motor 36. In the case of the illustrated embodiment incorporating a maltese-cross mechanism, this motor is preferably arranged to rotate the drive shaft through one revolution upon receipt of a signal from a programmed control unit.

When the plates 13 are clamped together between the pressure plates 19 and 22, with the aid of the bolts 18, the plates, together with the partition walls 15 mounted thereon, will define a plurality of channels or compartments 16, each being enclosed along its four sides and open solely at its peripheral ends. The channels 16 may also be arranged in a plurality of "floors", with the number of floors being equal to the number of plates in the plate pack. This is best seen from FIG. 3 of the drawings, which also illustrates a number of stoppers 14 located in respective channels. Because the channels 16 are arranged along evolvent lines on the plates, it is possible to place a maximum number of stoppers on each of the plates, so as to utilize the area of each plate optimally. This enables a very large number of stoppers to be accommodated in one plate pack of moderate dimensions. In order to provide ready access for washing liquid and steam to the stoppers in the channels, the plates 13, channels 16, are also provided with a large number of through-passing drainage holes, of which some are shown at 37 in FIG. 1.

Arranged along the inner surface of the chamber wall of the chamber part 2 are a number of peripherally extending, mutually parallel ribs 40, each of which is located in a plane extending perpendicular to the shaft 25. The number of such ribs will preferably be at least equal to the number of plates in the plate pack. The ribs guide rotation of the plate pack in the following manner. One or more dogging elements 41 are connected to the annular peripheral part 24 of the pressure plate 22, which assists in holding the plate pack together, and is provided with a recess 42 into which a rib 40 will fit. In order to guide said rotation in a positive fashion, a plurality of such dogging elements are preferably provided, and then preferably three such dogging elements, as illustrated in FIG. 1. Thus, when the recesses of the dogging elements are in engagement with a rib, the plate pack will be stationarily held in the axial direction while being freely rotatable, the dogging element recesses sliding along the ribs during rotation of the plate pack. As shown in the drawings, the ribs 40 will preferably have a square cross-section. Other cross-sectional shapes are possible, however, and it will be understood that the shape of the dogging element recesses 42 will be adapted to the cross-sectional shape of said ribs.

In order to enable the plate pack to be moved axially, the ribs 40 are provided with recesses 43 which are arranged at a pitch or spacing around the periphery commensurate with the positions of the dogging elements. The size of the recesses 43 in relation to the dogging elements may be such as to enable the dogging elements 41 to be moved axially past a rib, with a small amount of clearance, so as to be located opposite a following rib.

To facilitate axial movement of the dogging elements, the recesses 43 in the ribs 40 have arranged therein maneuvering devices 44 which are provided with ribs 45 similar to the ribs 40 disposed on the inner wall of the chamber. The number of maneuvering devices provided is equal to the number of dogging elements 41 and the number of recesses in the ribs 43. When dogging elements are located in the recesses 43 in the ribs, they are thus instead in engagement with the ribs 45 in the maneuvering devices 44.

Each of the maneuvering devices 44 is connected with one or more piston rods 46 each of which has connected at each end thereof pistons 47, 48 which move in corresponding cylinders 49, 50. The cylinders 49 and 50 are provided with connecting lines 51 and 52 respectively, for the introduction of a pressure fluid. Because the pressure fluid is introduced into one or the other of the cylinders 49 and 50, the associated piston 47 and 48 respectively can be moved in either one direction or the other, and move the maneuvering device connected to the piston rod 46 in the same direction. When the recess 42 of a dogging element 41 engages the ribs 45 on the maneuvering device 44, the whole of the plate pack can be moved in the axial direction.

Figure 3:
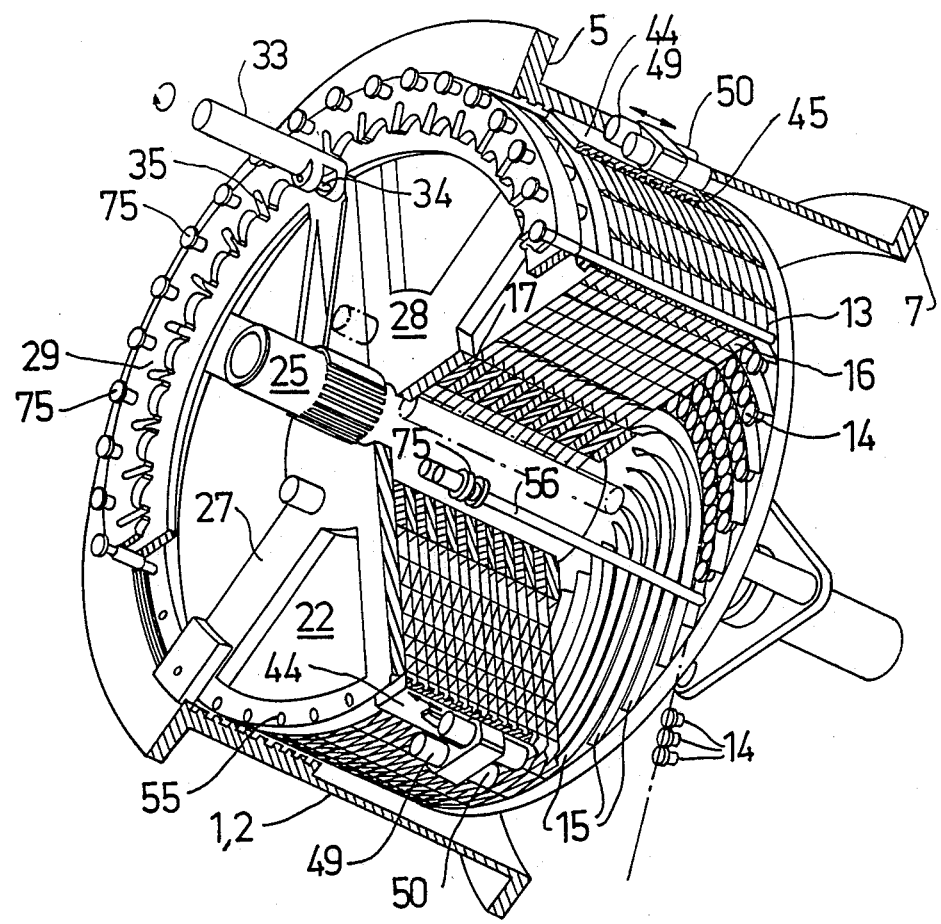
FIG. 3 is a perspective view, partly in section, of an inventive apparatus, the end walls of the chamber having been removed for the sake of clarity.

Each of the maneuvering devices co-acts with at least one piston rod with associated pistons and cylinders, and FIGS. 1 and 3 illustrate that two such arrangements may be provided for each maneuvering device.

The inlet opening 8 for stoppers to be washed and/or sterilized is located on the upper part of the chamber, so that the stoppers will fall gravitationally down into a channel 16. Similarly, the outlet opening 9 is disposed in the lower part of the chamber, so that the washed and/or sterilized stoppers will fall gravitationally from the channel 16, said stoppers then being advanced to the next process stage. This ensures that the stoppers are treated gently, so as to obviate all risk of deforming the stoppers. The stopper lines connected to the intake opening 8 and the outlet opening 9 are also provided with suitable valve means (not shown), which enable the stopper lines to be closed completely when desired, for instance when washing and sterilizing the stoppers.

Each of the plates 13 has provided in the peripheral opening of each of the channels 16 a plurality of holes 55 for receiving barrier rods 56. The holes 55 in the plates of the plate pack are mutually positioned in a line such as to enable the barrier rods 56 to be inserted through all of the holes corresponding to the position adjacent the periphery of the plates. Thus, the number of holes 55 and barrier rods 56 provided will be equal to the number of channels 16 in each of the plates 13. All of the barrier rods 56 will also pass through holes in the peripheral, annular part 24 of the pressure plate 22, therewith effectively guiding movement of the rods.

The purpose of the barrier rods 56 is to prevent stoppers located in a channel from falling therefrom and therewith impeding the function of the apparatus, for instance by being jammed between the plate pack and the inner surface of the chamber. It must be possible, however, to maneouver the barrier rods so that the peripheral opening of a channel can be exposed at the correct moment, when stoppers are to be introduced into the channel or discharged therefrom. To this end, the barrier rods are maneuvered by means of two maneuvering devices, generally referenced 57 and 58, which are mounted on one end wall 4 of the chamber at those positions of the chamber periphery at which the inlet opening 8 and the outlet opening 9 are located. The maneuvering devices 57 and 58 both have the form of pressure cylinders 59 and 60 provided with pistons 61 and 62, which are connected to piston rods 63 and 64. Pressure fluid can be introduced into respective cylinders on one side or the other of the pistons, through ports 65, 66 and 67, 68 respectively, so as to move the pistons backwards and forwards. The piston rods 63 and 64 extend through sealing lead-throughs or bushings 69 and 70 provided in the chamber end wall 41 and the ends of the piston rods located within the chamber are connected to dogging elements 71 and 72. The ends of respective dogging elements facing the plate pack are each provided with a respective recess 73 and 74, and the end of each barrier rod 56 facing towards the maneuvering devices is provided with a head 75, the circular edge of which fits into the recesses 73 and 74. Thus, when a barrier rod 56 is located opposite one of the maneuvering devices 57 and 58, the head 75 of said rod will engage the recess 73 or 74 and delivery of pressure medium to the piston, on one or the other side thereof, will result in forward or backward movement of the piston and therewith also in forward or backward movement of the barrier rod over the piston rod 63 or 64 and the dogging element 71 or 72. Mounted along the inner surface of the chamber is a peripheral, U-shaped guide rail 76. The heads 75 of respective barrier rods 56 can move freely around the cavity 77 of the U-shaped guide rail 76 as the plate pack rotates. Axial movement of the heads is prevented, however, by the limbs of the U. Consequently, a barrier rod can only be moved forwards or backwards when it is located opposite a maneuvering device 57 and 58. In the remaining positions of the barrier rods around the periphery of the plates, the cavity 77 in the guide rail 76 will force the barrier rods 56 to maintain their set position in the axial direction. The various functions oF the apparatus and the mutual order of said functions are controlled by a programmed unit (not shown), as hereinafter described.

The apparatus is preferably constructed from a material capable of withstanding the conditions which prevail when washing and sterilizing the articles and which can also itself be easily sterilized in accordance with pharmaceutical practice. Stainless steel has been found a suitable material in this respect, although if more drastic conditions can be expected to prevail, the apparatus may be constructed from such material as titanium.

Figure 2:
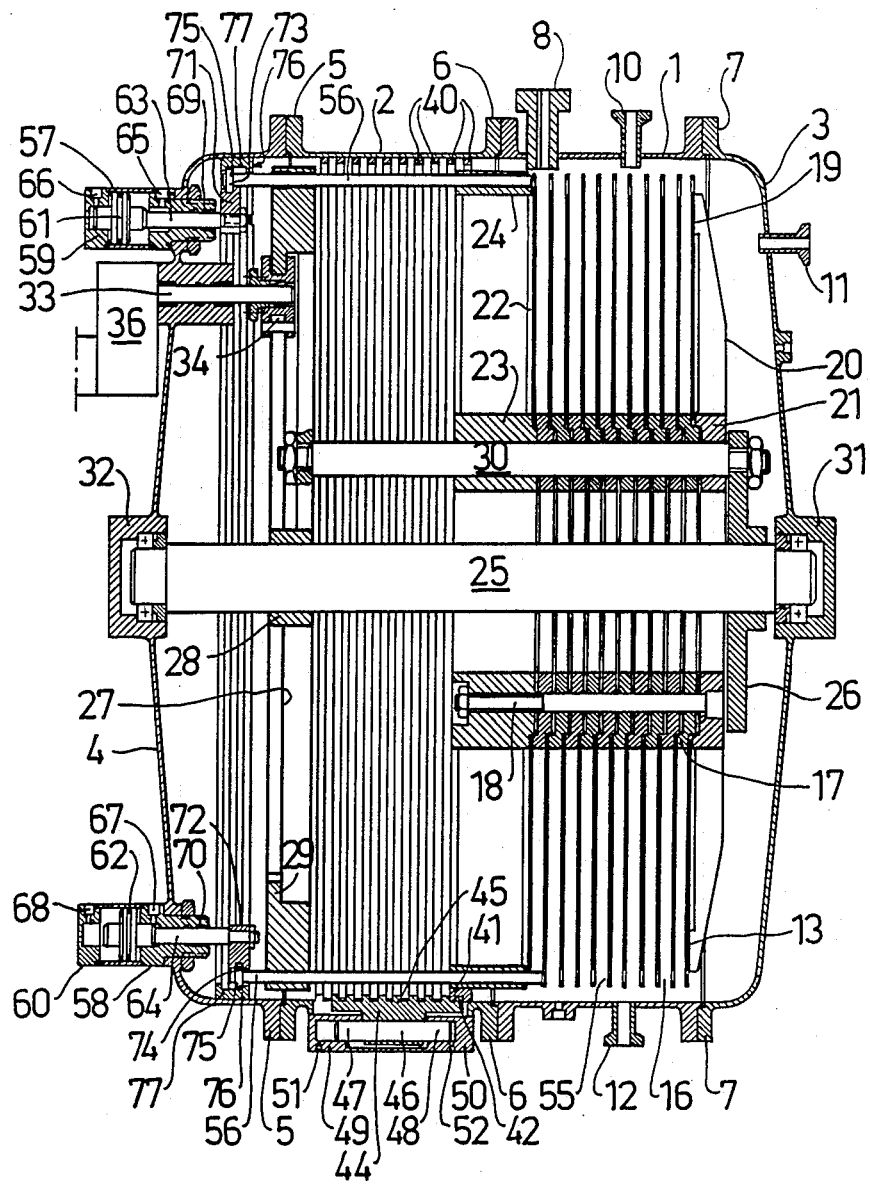
FIG. 2 is an axial or longitudinal sectional view taken on the line A—A in FIG. 1.

The modus operandi of the apparatus is as follows:

The apparatus is completely empty of stoppers in its starting mode, and the plate pack 13 is located in its right-hand terminal position along the shaft 25, as illustrated in FIG. 2. A channel 16 on the plate of said plate pack located nearest the left-hand side is positioned opposite the stopper inlet opening 8. At this stage, all barrier rods 56 occupy a position in which they close the channels 16 in the plate 13 located opposite the inlet opening 8.

The programmed unit now produces a signal which results in the introduction of pressure fluid into the pressure cylinder 59, through the port 65, such as to move the piston 61 rearwardly in the cylinder, and therewith also the piston rod 63 and the dogging element 71 connected therewith. Because the head 75 at the end of the barrier rod 56 is in engagement with the recess 73 in the dogging element 71, the barrier rod 56 will also be moved rearwardly. Consequently, the other end thereof will be withdrawn axially from the channel 16 in the vicinity of its peripheral opening, so as to expose the opening and allow stoppers to be introduced into the channel.

Properly positioned stoppers 14 are now introduced through the inlet opening 8, until the channel 16 is filled. The supply of stoppers to the channel can be controlled by a counter provided with a photocell (not shown) and being constructed to count the number of stoppers delivered to the channel and to interrupt the delivery of stoppers when the desired number of stoppers has been introduced into the channel. The stoppers are introduced into the channel purely gravitationally, so as to ensure that the stoppers will be treated gently.

When the channel has been filled, the programmed unit produces a signal which causes pressure fluid to be introduced into the pressure cylinder 59, through the port 66, at the same time as pressure fluid is able to flow out through the port 65. This will cause the piston 61 to move forwards, and since the piston 61 is connected to the barrier rod 56, as beforementioned, the barrier rod will also be moved forwards and into the channel 16 in the vicinity of its peripheral opening. The barrier rod 56 will therewith block the channel opening, so as to prevent the stoppers located in the channel from falling out.

When the barrier rod 56 has been moved forwards to its channel closing position, the programmed unit sends a signal to the drive motor 36 for rotation of the drive shaft 33 through one complete revolution. This rotation of the drive shaft causes the drive pin 34 to engage in an indent 35 in the internal gear ring 29, so that the plate pack is rotated through one step, such that a following channel 16 will be located opposite the article inlet opening 8 and such that its corresponding barrier rod 56 is connected with the maneuvering device 57. When this stage of operation has been reached, the programmed unit produces a further signal which causes pressure fluid to be introduced through the port 65 in the pressure cylinder 59 and conducted out through the port 66, so as to withdraw the piston 61 together with the piston rod 63 and the dogging element 71 and therewith, in the aforedescribed manner, causing the barrier rod 56 to be withdrawn so as to expose the peripheral opening of the channel 16, which is now located opposite the outlet opening 8.

In response to a signal from the programmed unit, the channel which is now located opposite the inlet opening is filled with orderly positioned stoppers 14, and subsequent to introducing the desired number of stoppers into the channel, the supply of stoppers is interrupted and the associated barrier rod 56 is maneuvered by means of the maneuvering device 57 in the aforedescribed manner, so as to again block the channel at its peripheral opening. The plate pack is then rotated through a further step, the opening of a newly positioned channel is exposed by withdrawing a corresponding barrier rod, and a following channel is filled with stoppers and blocked off in the manner aforedescribed.

The barrier rods 56 are thus always in a channel blocking or closing position, with the exception of when stoppers are to be introduced into a channel or removed therefrom, in which instances the barrier rod belonging to this specific channel is maneuvered in a manner to expose the peripheral opening of said channel.

Rotation of the plate pack is controlled by means of the dogging elements 41, the respective recesses 42 of which are in engagement with a rib 40 extending peripherally around the inside of the chamber wall. This will prevent the plate pack from being moved axially, while still enabling the plate pack to be freely rotated.

Subsequent to filling all channels or compartments 16 on one plate with stoppers, the plate pack shall be located in a position such that its dogging element 41 is located opposite the recesses 43 in the ribs 40 and instead engages the maneuvering devices 44, located in the recesses 43, and their corresponding ribs 45. The programmed unit now produces a signal which causes pressure fluid to be introduced into the pressure cylinder 50 through the connecting line 52, so that the piston 48 will be axially displaced rearwardly to an extent which corresponds to the distance between two mutually adjacent plates in the plate pack. Because the piston rod 46 is connected with the maneuvering device 44 and because the ribs 45 of said device are in engagement with the recess 42 in the dogging element 41, the plate pack will also be moved rearwardly in an axial direction to an extent corresponding to the distance between two mutually adjacent plates in the plate pack. Continued rotation of the plate pack will cause the dogging elements 41 with the recesses 42 to come into engagement with a following peripheral rib 40 on the inside of the chamber wall, and therewith fixate the pack in a new axial position, in which the plate pack can still be freely rotated.

When the plate pack has been rotated to an extent such that its dogging element 41 is no longer connected with the maneuvering devices 44, the devices are returned to their earlier position, by introducing pressure fluid into the pressure cylinder 49, through the connecting line 51, so as to return the piston 47 to its original position. The maneuvering devices 44 are now in a position in which the plate pack can be moved through a further step axially in a rearward direction, subsequent to rotating the plate pack through one complete revolution and- having filled with stoppers the channels in the plate which is now located on the same level as the inlet opening 8, in the same manner as that described in the aforegoing.

When the plate pack is moved axially through one step, the barrier rods 56 will remain in their respective positions relative to the inlet or infeed opening 8. The rods 56 will therewith be located in a channel blocking position relative to the channels to be filled in the following plate, and with the filling of each channel in said plate the barrier rods will be first maneuvered to a position in which access can be had to the channel and, subsequent to filling the channel, will be maneuvered to a channel closing position, by means of the maneuvering device 57, in the manner aforedescribed. The filled channels of the preceding plate are constantly held blocked, so that no stoppers can fall from the channels.

The channels are thus filled successively in each of the plates, in the aforedescribed manner whereafter the plate pack is moved axially through one step, so that the channels in an immediately following plate can be filled. Washing and sterilizing of the stoppers can be commenced, subsequent to filling all of the channels 16 in the plate pack with stoppers, or subsequent to filling a desired number of said channels.

The maneuvering device 58 has remained inactive during the whole of the aforedescribed filling process, and the heads of the barrier rods have passed the dogging element 72 associated with said maneuvering device, without being moved in the axial direction. The maneuvering device 58 is not activated until the washed and sterilized stoppers are to be removed from the apparatus.

When washing and sterilizing the stoppers, a washing liquid, normally hot water, is introduced through one of the connections 10, 11 and 12. The inlet opening 8 and the outlet opening 9 are sealed in a gas-tight fashion with the aid of suitable valves (not shown), prior to introducing said washing liquid. When washing and rinsing of the stoppers is completed, washing and rinsing liquid is discharged through an outlet, e.g. 12, before sterilization of the stoppers is commenced. The stoppers are preferably sterilized with steam, at a temperature of at least about 120° C. Consequently, the apparatus chamber must be effectively sealed and capable of withstanding the necessary steam pressure.

Because the plates 13 incorporate a large number of throughpassing drainage holes 37, the washing and rinsing liquids and the sterilizing steam can readily penetrate throughout the entire pack of plates and therewith act upon all of the stoppers located thereon.

The plate pack is preferably rotated throughout the washing, rinsing, and sterilizing processes, so that the treatment will be as effective as possible. This rotation of the plate pack is obtained in response to requisite control signals which activate the drive motor 36 with drive shaft 33. Although the described embodiment includes a maltese-cross stepping mechanism, such that rotation is effected stepwise, embodiments provided with conventional gear rings and continuous rotation during the treatment processes are conceivable.

Because the channels of the inventive apparatus are configured as evolvent lines, during rotation of the plate pack each stopper will move in a manner to be separated from mutually adjacent stoppers twice with each full revolution. In this respect, the degree of movement can be varied, for instance, by varying the number of stoppers introduced into each channel. This movement of the stoppers means that the total surface area of the stoppers will be exposed to the washing and sterilizing media, therewith enhancing the effect of the treatment. The stoppers are also prevented, at the same time, from adhering to one another and therewith being deformed or having pieces or particles removed therefrom as a result of mutual contact. This represents an important advantage afforded by the invention.

Subsequent to sterilizing the stoppers, the stoppers are cooled to a suitable temperature, by introducing a cooling fluid, such as sterile water, or an inert and sterile gas, such as nitrogen. The conditions can also be selected so that the stoppers will dry while retaining their sterility. The stoppers can now be stored in the apparatus under sterile conditions, and subsequently removed therefrom at desired times, for stoppering of bottles.

When the sterilizing process has been completed and the stoppers are to be removed from the apparatus, the plate pack will be located in its furthest withdrawn position, nearest the drive wheel 27, as illustrated in FIG. 3. At the same time, the leading plate 13 located furthest to the right of the plate pack, together with the channels or compartments 16 on said plate (FIG. 2) will be located opposite the stopper outlet opening 9. All of the barrier rods 56 will be located in their forwardly displaced positions in the plate pack, so as to block the openings in all channels 16 and prevent stoppers falling from the channels.

At this stage of apparatus operation, the programmed unit produces a signal which causes pressure fluid to be introduced into the pressure cylinder 60, through the port 67, so that the piston 62 will be moved rearwardly to an extent corresponding to the distance between two mutually adjacent plates in the plate pack. Consequently, the piston rod 64 and the dogging element 72 connected therewith will also be moved rearwardly and since the head 75 on the barrier rod 56 is in engagement with the recess 74 in the dogging element 72, the barrier rod 56 will also be withdrawn to an extent such as to expose the peripheral opening of the channel 16. The stoppers 14 are then able to roll out gravitationally through the outlet opening 9 and pass along the stopper line connected therewith and enter a bottle stoppering arrangement. Similar to the case of the stopper inlet opening 8, a counter provided with a photocell (not shown) may also be positioned adjacent the outlet opening 9, this counter being effective in counting the number of stoppers passing the outlet and in sending a control signal to the programmed unit when a desired number of stoppers have rolled from the apparatus.

In response to this control signal the programmed unit produces a signal which causes pressure fluid to be introduced into the cylinder 60 through the port 68, while at the same time discharging pressure fluid through the port 67. The piston 62 is therewith moved forwards, together with the piston rod 64 and the dogging element 72. The recess 74 of the dogging element 72 is connected with the head 75 of the barrier rod 56, and consequently the barrier rod will be returned to its channel closing position.

When the peripheral opening of the channel has been blocked off, the programmed unit will send a signal to the drive motor 36, causing the drive shaft 33 to be rotated through one revolution. As a result of this rotation, the drive pin 34 will engage an indent 35 in the gear ring 29, so as to rotate the entire plate pack through one step, therewith bringing the following channel 16 into position opposite the outlet opening 9. A further signal is then sent from the programmed unit, so as to cause the barrier rod 56 associated with said opening 9 to be withdrawn in the aforedescribed manner, such as to expose the peripheral opening of said channel. The stoppers 14 located in said channel are then able to roll out of the channel in the aforedescribed manner, and exit through the outlet opening 9 and pass to the bottle stoppering arrangement. When this particular channel is empty, a further signal is produced by the programmed unit, in the aforedescribed manner, causing the barrier rod 56 to be returned to its channel closing position, and the plate pack is rotated through a further step, so as to bring a further channel 16 into register with the outlet opening 9. The barrier rod 56 associated with said further channel is then withdrawn, so that the stoppers located in said further channel are able to roll therefrom. This sequence of events is repeated, until all channels 16 on a plate 13 have been emptied of stoppers.

The plate pack is guided during its rotation by means of the dogging elements 41, the respective recesses 42 of which have been in engagement with the peripheral ribs 40 located furthest to the rear along the inner wall of the chamber. Consequently, the plate pack has been prevented from moving axially while being freely rotatable. When all of the channels 16 on the leading plate have been emptied, the plate pack shall be located in a rotational position such that its dogging element 41 is located in the recesses 43 on the ribs 40, and will thus not engage any of the ribs. Instead, the dogging element recesses 42 engage the corresponding ribs 45 in the maneuvering or auxiliary devices 44, which have been earlier moved to their rearmost position by the piston rod 46 and the piston 50.

At this stage of operation, the programmed unit produces a control signal which causes pressure fluid to be introduced through the connecting line 51 in the pressure cylinder 49, so that the piston 47 and the piston rod 46 will be moved forwards through a distance corresponding to the distance between two mutually adjacent plates 13. Because the piston rod 46 is connected to the maneuvering device 44, the plate pack will also be moved forwards through a similar distance, via the dogging element 41, so that the channels or compartments on a following plate will be brought to the same level as, or in register with the outlet opening 9. The barrier rods 56 do not accompany this axial movement of the plate pack, but remain axially stationary. Consequently, when a following plate has been moved into a stopper discharge position, the barrier rods will block all of the peripheral openings of the channels on this plate.

Stoppers located in the channels of the plate now in register with the outlet opening 9 are discharged from the channels in the same manner as the stoppers in the preceding plate, by withdrawing in sequence the barrier rod located opposite the outlet opening through one step, so that the stoppers are able to fall from the channel, whereafter the barrier rod is returned to its channel closing position and the plate pack is rotated through a further step and the barrier rod which blocks the following channel is withdrawn. This sequence of events is repeated until all channels or compartments on the plate concerned have been emptied of stoppers. The entire plate pack is then moved forwards through a further step in the axial direction, in the manner aforedescribed. This process can be repeated until the channels of all plates in the pack have been emptied of stoppers. The plate pack will now be located in a position in which it can be refilled with stoppers, in the aforedescribed manner, followed by washing and sterilizing of the stoppers. If considered suitable, the interior of the apparatus can also be washed subsequent to discharging the stoppers therefrom and prior to introducing further stoppers thereinto. It will be understood that the sequence of filling the apparatus with stoppers, washing and sterilizing the stoppers and emptying the plate pack of stoppers can be repeated as often as desired.

Normally, two or preferably three inventive apparatus are connected together in parallel to form a battery or assembly which is connected on the input side thereof to an apparatus for positioning the stoppers in an ordered array and for introducing the stoppers into the inventive apparatus, and which on the output side thereof is connected to a downstream bottle stoppering apparatus. With two such apparatus connected in parallel, one apparatus can be filled with stoppers which are then washed and sterilized, while simultaneously discharging sterile stoppers to the bottle stoppering apparatus from the other of said apparatus. With three inventive apparatus connected in parallel, a first apparatus can be filled with stoppers while, at the same time, washing and sterilizing stoppers in a second apparatus, while, at the same time, discharging sterilized stoppers from a third apparatus. The programmed unit can be constructed to connect the different apparatus to the stopper infeed mode and stopper outfeed mode respectively at the correct time points, with the aid of suitable, known switching devices. This will ensure continuous availability of sterile and orderly positioned stoppers for a following apparatus in which bottles are filled and stoppered under sterile conditions.

The inventive apparatus has been described in the aforegoing primarily with respect to its function of washing and sterilizing bottle stoppers. It will be obvious to those skilled in this art, however, that the apparatus may also be used for washing and sterilizing capsules or caps, and that only minor modifications need be made to the apparatus for this purpose.

The fact that only simple modifications need be made to the inventive apparatus in order to enable the apparatus to treat stoppers or capsules of mutually different sizes represents a further important advantage. It is often only necessary in this case to replace the plate pack of the apparatus with another plate pack whose channels have been dimensioned to accommodate sealing devices of other dimensions. It may sometimes be necessary in this respect to change also the arrangement of ribs 40 on the inside of the chamber, although this change can also be effected relatively simply, since the chamber is divided into several parts, so that only the chamber part 2 in which the ribs are mounted need be exchanged.

In order to enable the inventive apparatus to operate correctly, the apparatus includes a number of ancillary devices and machine elements, such as valves, pipes, pumps and measuring and sensing devices. The function and construction of these devices and machine elements are conventional and said devices and elements are readily available commercially. The skilled person who is aware of the desired function will have no difficulty in selecting ancillary devices of suitable construction and design.

One significant ancillary device is the master programmed unit which controls the operation of the various parts of the apparatus. Control signals for starting the various functions of the apparatus at the correct time points and for correctly positioning the working components of the apparatus are produced and delivered in response to input signals from different sensing and measuring devices. Such programmed units are well known and will normally include a plurality of integrated circuits, all of which are readily accessible commercially. The skilled person will find no difficulty in constructing a suitable programmed unit when having knowledge of the functions desired, and consequently it is not necessary to describe the programmed unit in detail.

In the aforegoing, the inventive apparatus has been described with reference to the accompanying drawing primarily with respect to the washing and sterilizing of stoppers or capsules, preferably with hot water and steam. It will be understood, however, that the inventive apparatus is not restricted solely to this use, but can be used generally for treating a plurality of mutually similar articles with liquid and/or gaseous medium, while constantly affording the advantages of effecting such treatment in isolation from the surroundings and in a simple and effective manner. For example, the inventive apparatus can be readily modified for use for chemically treating a plurality of similar articles with a chemical agent, for instance an impregnating agent. Furthermore, the apparatus can be used for sterilizing articles with medium other than steam, e.g. with alcohol or ethylene oxide. It will also be understood by those skilled in this art that further modifications and variants of the inventive apparatus are possible within the scope of the following claims.

I claim:

1. Apparatus for treating a plurality of articles with at least one fluid medium, said apparatus comprising a substantially cylindrical chamber which is provided with an article inlet opening and an article outlet opening, and further including at least one article holder device mounted in the chamber and intended for holding an ordered array of articles to be treated, each holder device has the form of a circular plate which has mounted thereon guide devices which comprise partition walls which are so arranged as to define channels or compartments in which the articles are arranged in rows along evolving lines extending from the centre of the plate to the periphery thereof; the plate being arranged to be rotated stepwise about a horizontal axis which is concentrical with the cylindrical chamber and perpendicular to the plate, such that the channels can be brought singly into communication with the article inlet opening or the article outlet opening.

2. Apparatus according to claim 1, characterized in that a plurality of plates are combined to form a plate pack such that a side of a plate which has no partition walls thereon faces a side of an adjacent plate on which partition walls are provided.

3. Apparatus according to claim 2, characterized in that said apparatus is provided with means for moving the plate pack stepwise in the axial direction, each such step corresponding to the distance between two mutually sequential plates.

4. Apparatus according to claim 1, characterized in that mutually parallel ribs are mounted peripherally around the inner wall of the chamber; and in that at least one dogging element connected with the plates is arranged for engagement with said ribs in a manner to fixate the plates axially while permitting rotation of said plates.

5. Apparatus according to claim 4, characterized in that the ribs incorporate recesses where the dogging element and plates connected therewith can be moved axially, with the aid of a maneuvering device, into engagement with a following rib.

6. Apparatus according to claim 1, characterized in that the apparatus is provided with movable barrier devices which close those channels into which articles are not to be introduced or from which articles are not to be removed.

7. Apparatus according to claim 6, characterized in that the barrier devices have the form of barrier rods which extend axially through holes in the plates located adjacent the peripheral opening of each of the channels; and in that said rods can be moved axially to expose or to block the opening of a given channel.

* * * * *